US00PP30328P3

(12) United States Plant Patent
Sidhu

(10) Patent No.: US PP30,328 P3
(45) Date of Patent: Apr. 2, 2019

(54) ***COTINUS* PLANT NAMED 'COTSIDH5'**

(50) Latin Name: *Cotinus coggygria*
Varietal Denomination: Cotsidh5

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 15/932,382

(22) Filed: Feb. 20, 2018

(65) Prior Publication Data

US 2018/0279527 P1 Sep. 27, 2018

(30) Foreign Application Priority Data

Mar. 27, 2017 (CA) ..... PBR 17-9154

(51) Int. Cl.
*A01H 5/00* (2018.01)
*A01H 6/00* (2018.01)
*A01H 5/12* (2018.01)

(52) U.S. Cl.
USPC ..... Plt./226
CPC ..... *A01H 6/00* (2018.05); *A01H 5/00* (2013.01); *A01H 5/12* (2013.01)

(58) Field of Classification Search
USPC ..... Plt./226, 216
CPC ..... A01H 5/00; A01H 5/02
See application file for complete search history.

*Primary Examiner* — Kent L Bell
(74) *Attorney, Agent, or Firm* — Penny J. Aguirre

(57) ABSTRACT

A new cultivar of *Cotinus coggygria*, 'Cotsidh5', that is characterized by its new foliage that is very small in size before maturing in 2 to 3 weeks, its purple foliage, and its very compact growth habit.

2 Drawing Sheets

Botanical classification: *Cotinus coggygria.*
Variety denomination: 'Cotsidh5'.

BACKGROUND OF THE INVENTION

The present invention relates to a new and distinct cultivar of *Cotinus coggygria* and will be referred to hereafter by its cultivar name, 'Cotsidh5'. 'Cotsidh5' is a new cultivar grown for use as a landscape plant.

The new cultivar arose as a chance seedling that was growing in a container in a container bed of *Cotinus coggygria* 'Royal Purple' (not patented) in spring of 2011 in Mission, British Columbia, Canada. 'Royal Purple' is thought to be a parent based on the characteristics of the new cultivar and its proximity.

Asexual propagation of the new cultivar was first accomplished under the direction of the inventor by tissue culture of meristematic tissue in July of 2011 in Mission, British Columbia, Canada. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Cotsidh5' as a unique cultivar of *Cotinus.*

1. 'Cotsidh5' exhibits new foliage that is very small in size before maturing in 2 to 3 weeks.
2. 'Cotsidh5' exhibits purple foliage.
3. 'Cotsidh5' exhibits a very compact growth habit.

'Royal Purple', the probable parent plant of 'Cotsidh5', is similar to 'Cotsidh5' in foliage color. 'Royal Purple' differs from 'Cotsidh5' in having a much less compact plant habit. 'Cotsidh5' can be compared to the *Cotinus coggygria* cultivar 'Young Lady' (not patented). 'Young Lady' is similar to 'Cotsidh5' in growth habit and plant size. 'Young Lady' differs from 'Cotsidh5' in having foliage that is green in color.

BRIEF DESCRIPTION OF THE DRAWINGS

The accompanying colored photographs illustrate the overall appearance and distinct characteristics of the new *Cotinus*. The plants in the photographs are 3-years in age as grown outdoors in 1-gallon containers in St. Thomas, Ontario, Canada.

The photograph in FIG. 1 illustrates the overall plant habit and foliage coloration of 'Cotsidh5' in summer.

Figure 1:
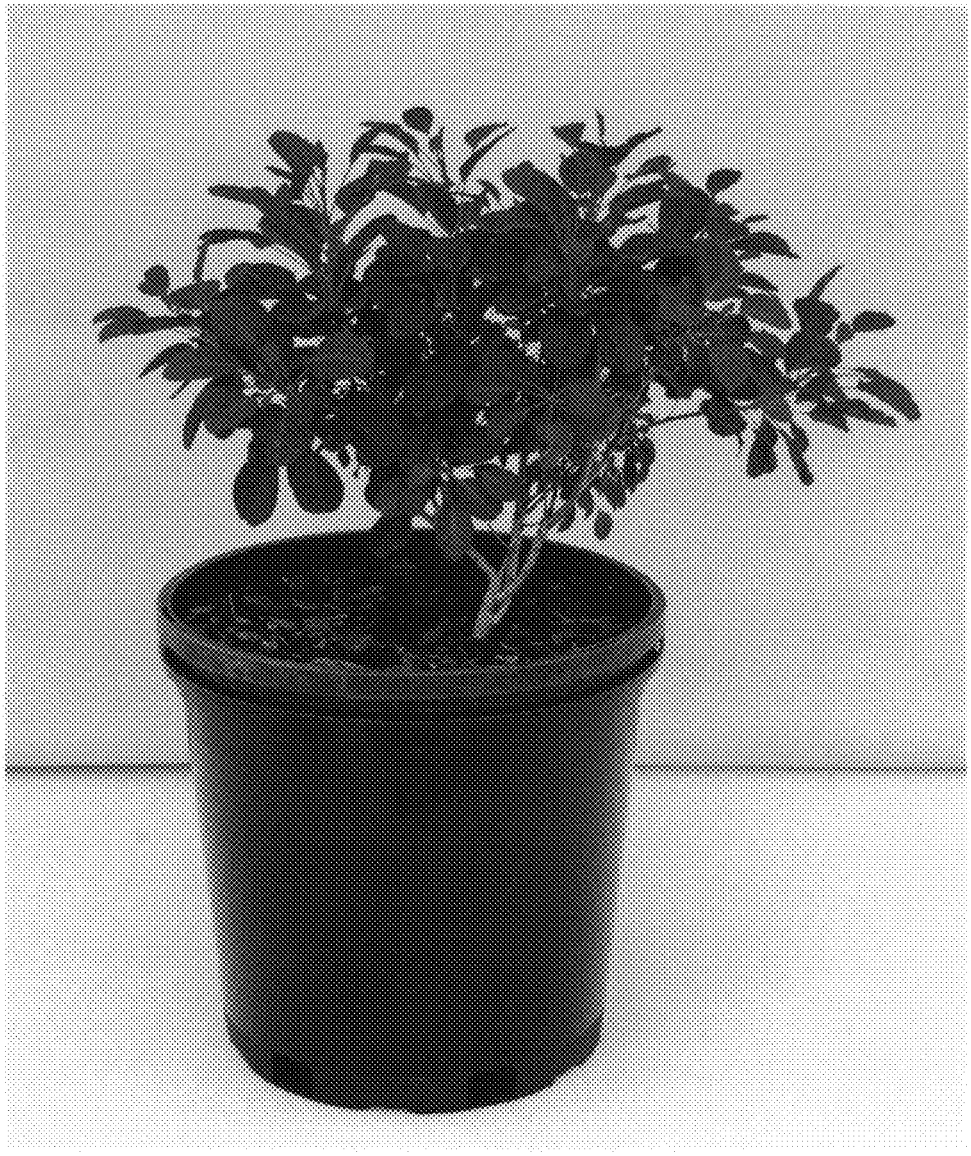
Figure 2:
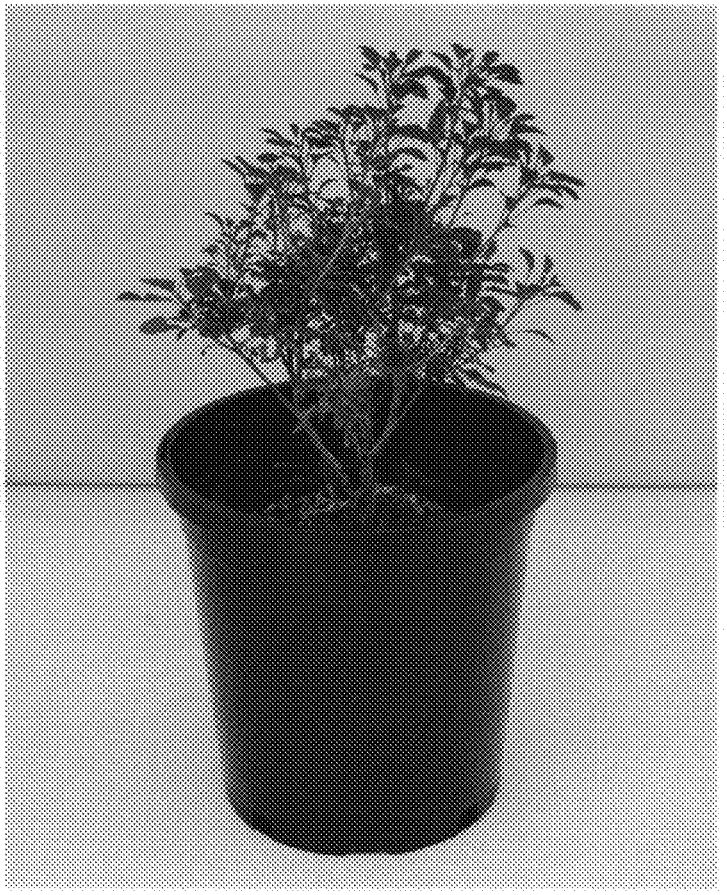

The photograph in FIG. 2 provides a view of the new foliage in spring of 'Cotsidh5'.

Figure 3:
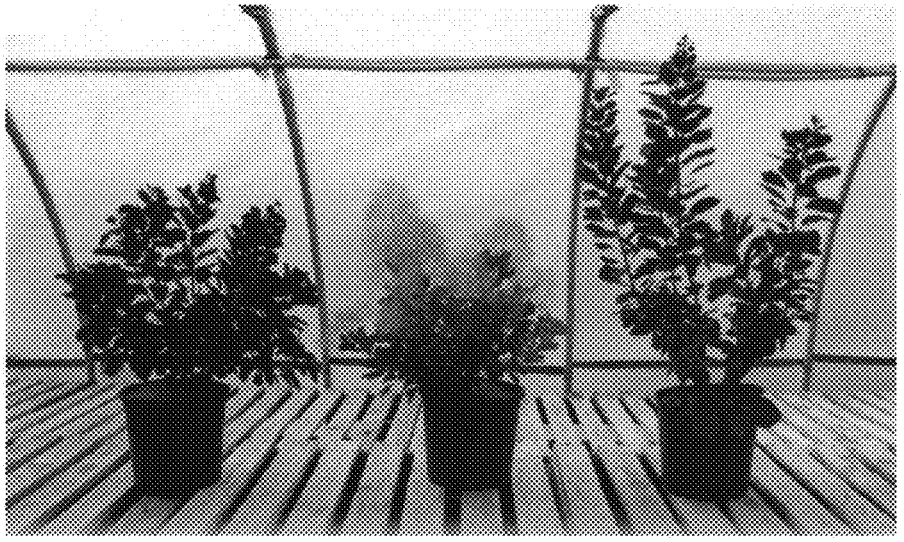

The photograph in FIG. 3 provides a comparation between 'Cotsidh5' (left), 'Young Lady' (middle), and 'Royal Purple' (right).

The colors in the photographs are as close as possible with the digital photography techniques utilized and the color values cited in the detailed botanical description accurately describe the colors of the new *Cotinus.*

DETAILED BOTANICAL DESCRIPTION

The following is a detailed description of 3 year-old plants of the new cultivar as grown outdoors in a 1-gallon container in St. Thomas, Ontario, Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Small flowers are present in June with the inflorescences becoming showy as the pedicels become villose from mid July to mid August.

*Plant habit*.—Broadly rounded, very compact.

*Height and spread*.—Plants 3 years in age reach on average 56 cm in height and 67 cm in width.

*Cold hardiness*.—At least in U.S.D.A. Zone 4.

*Diseases and pests*.—No susceptibility or resistance to diseases or pests have been observed.

*Root description*.—Fibrous.

*Propagation*.—Tissue culture preferred.

*Root development*.—Root intiate in about 6 weeks and a young rooted plant is produced in about 2 years.

*Growth rate*.—Slow.

Branch description:

*Branch shape*.—Round.

*Branching*.—Multi-stemmed, average of 4 lateral branches each having on average of 2 secondary branches, alternate or whorled if pinched in production.

*Branch color*.—Young stem (shoot); 187A to 187B in color with vertical, round or oval shaped lenticels, 155B in color (about 30 per square cm), mature stem; 199D in color with fissures 200A in color and horizontal in aspect, cylindrical shape, lenticels 164D in color (about 15 per square cm).

*Branch size*.—Main stem; average of 3 cm in length and 1.4 cm in width, lateral branches; average of 55.1 cm in length and 5 mm in width, secondary branches; average of 26.1 cm in length and 4 mm in width.

*Stem surface*.—Main stem and lateral branches are finely barked with horizontal weakly protruding lenticels, secondary and tertiary branches (twigs) are smooth, glabrous, and semi-glossy, covered with numerous lenticels.

*Internode length*.—Lateral branch; average of 2.3 cm in length, secondary and tertiary branch; average of 1 cm in length.

Foliage description:

*Leaf shape*.—Orbicular.

*Leaf division*.—Simple.

*Leaf base*.—Rounded.

*Leaf apex*.—Obtuse to rounded.

*Leaf fragrance*.—None.

*Leaf venation*.—Pinnate, conspicuous, midrib on upper surface 184B to 184C in color, midrib on lower surface between 138B and 138C with a strong overlay of 183D in color, lateral veins on upper surface 184B to 184C in color, lateral veins on lower surface 185C.

*Leaf margins*.—Entire and slightly undulate.

*Leaf arrangement*.—Spiral and alternate.

*Leaf attachment*.—Petiolate.

*Leaf surface*.—Upper surface; weak glossiness, medium glaucosity, and glabrous, lower surface; dull and glabrous.

*Leaf size*.—Variable, average of 6.6 cm in length and 5 cm in width.

*Leaf quantity*.—About 20 per secondary branch.

*Leaf color*.—Spring; emerging leaves upper and lower surface color; 185A, summer; middle plant canopy; upper surface 200A (but greener), lower surface 147B, lower plant canopy; upper surface 147A, lower surface 147B, fall; upper and lower surfaces may exhibit the following range of colors 187A, 147A, 24D, 29A to 29B, 34C, and 44C to 44D.

*Petioles*.—Glabrous, average of 4 cm in length and 4 mm in width, distal half on upper surface N199A with strong overlay of 185B in color, basal half on upper surface more yellow than 144D with a light overlay of 181D in color, lower surface more yellow than 144D in color.

*Stipules*.—Absent.

Inflorescence description:

*Inflorescence type*.—Thyrse compound open pyramidal-shaped panicles on terminals of lateral branches and twigs, flowers are small and non-showy with the pedicels expanding and becoming plumose-villose and showy in mid summer.

*Inflorescence size*.—Average of 16 cm in length and 9 cm in width before dehiscence.

*Rachis*.—Average of 14 cm in length and 2 mm in width, average internode length is 2 cm, secondary branches an average of 3 cm in length and 1 mm in width, surface is glabrous, redder than 200A in color.

*Pedicels*.—At flowering; about 3 mm in length and 0.4 mm in width, redder than 200A in colour.

*Flower buds*.—Round to broadly ovate in shape, 3 mm in depth and 4 mm diameter, redder than 200A.

*Flower fragrance*.—None.

*Lastingness of flowers*.—True flowers are short lived (less than one week) with showy pedicels lasting about one month with good color and fading in color but persisting into fall.

*Flower quantity*.—About 200 per compound inflorescence.

*Flower type*.—Star-shaped, rotate.

*Flower aspect*.—Upright on pedicels.

*Flower size*.—About 7 mm in diameter and 4 mm in depth.

*Petals*.—5, about 3 mm in length and 2 mm in width, un-fused and spreading, elliptic shape, cuneate, acute apex, glabrous surface, blend of 193A and 145C in color.

*Sepals*.—5, about 1.7 mm in length and 1 mm in width, fused at base, acute apex, pubescent surface, redder than 200A in color.

Reproductive organs:

*Pistils*—1, style; 1.5 mm in length, stigma; 0.2 mm in width, 145A in color, ovary; superior, about 3 mm in length and width, 3-carpelled, 143A in color.

*Stamens*.—5, filament; 1.0 mm in length, anther; 1.3 mm in length and 0.6 mm in width, 6C in colour.

*Fruit and seed*.—None observed to date.

It is claimed:

1. A new and distinct cultivar of *Cotinus* plant named 'Cotsidh5' as herein illustrated and described.

* * * * *